US010806604B2

(12) United States Patent
Caldwell et al.

(10) Patent No.: US 10,806,604 B2
(45) Date of Patent: Oct. 20, 2020

(54) VACUUM PUMP SYSTEMS FOR PROSTHETIC LIMBS AND METHODS OF USING THE SAME

(71) Applicant: Northwestern University, Evanston, IL (US)

(72) Inventors: Ryan J. Caldwell, Long Grove, IL (US); Matthew J. Major, Chicago, IL (US)

(73) Assignee: Northwestern University, Evanston, IL (US)

( * ) Notice: Subject to any disclaimer, the term of this patent is extended or adjusted under 35 U.S.C. 154(b) by 231 days.

(21) Appl. No.: 15/756,839

(22) PCT Filed: Aug. 19, 2016

(86) PCT No.: PCT/US2016/047775
§ 371 (c)(1),
(2) Date: Mar. 1, 2018

(87) PCT Pub. No.: WO2017/040068
PCT Pub. Date: Mar. 9, 2017

(65) Prior Publication Data
US 2018/0271679 A1  Sep. 27, 2018

Related U.S. Application Data

(60) Provisional application No. 62/214,560, filed on Sep. 4, 2015.

(51) Int. Cl.
*A61F 2/70* (2006.01)
*A61F 2/80* (2006.01)
*A61F 2/74* (2006.01)

(52) U.S. Cl.
CPC .................. *A61F 2/70* (2013.01); *A61F 2/80* (2013.01); *A61F 2002/742* (2013.01); *A61F 2002/802* (2013.01); *A61F 2002/807* (2013.01)

(58) Field of Classification Search
CPC . A61F 2/80; A61F 2002/742; A61F 2002/807
See application file for complete search history.

(56) References Cited

U.S. PATENT DOCUMENTS 4,161,042 A   7/1979 Cottingham et al.
5,724,714 A   3/1998 Love
(Continued)

OTHER PUBLICATIONS

International Search Report and Written Opinion for PCT/US2016/047775 dated Dec. 5, 2016.
(Continued)

*Primary Examiner* — Christie L Bahena
(74) *Attorney, Agent, or Firm* — Banner & Witcoff, Ltd.

(57) ABSTRACT

Pump systems for use in suspension of a prosthetic device from a residual limb and methods of suspending a prosthetic device from a residual limb are disclosed. The pump systems include a mechanically activated pump having a first compression member coupled to a second compression member, a diaphragm disposed between the first and second compression members, and coupling elements that engage and couple together the first and second compression members. The mechanically activated pump may be connected with an electrically activated pump, forming a hybrid pump system to provide vacuum engagement between a prosthetic device and a residual limb.

10 Claims, 8 Drawing Sheets

(56) References Cited

U.S. PATENT DOCUMENTS

| | | | |
|---|---|---|---|
| 5,931,872 | A | 8/1999 | Lohmann |
| 6,761,742 | B2 | 7/2004 | Caspers |
| 7,025,792 | B2 | 4/2006 | Collier |
| 7,744,653 | B2 | 6/2010 | Rush et al. |
| 7,947,085 | B2 | 5/2011 | Haines et al. |
| 8,007,543 | B2 | 8/2011 | Martin |
| 8,308,816 | B2 | 11/2012 | Slemker et al. |
| 9,066,822 | B2 | 6/2015 | Caldwell et al. |
| 9,757,255 | B2 | 9/2017 | Caldwell et al. |
| 2002/0099450 | A1 | 7/2002 | Dean, Jr. et al. |
| 2005/0149202 | A1 | 7/2005 | Schaffer et al. |
| 2005/0278039 | A1 | 12/2005 | Nobbe |
| 2007/0055383 | A1 | 3/2007 | King |
| 2007/0112439 | A1 | 5/2007 | Panucialman |
| 2007/0213839 | A1 | 9/2007 | Nachbar |
| 2008/0221706 | A1 | 9/2008 | Scussel et al. |
| 2008/0269911 | A1 | 10/2008 | Street et al. |
| 2009/0000011 | A1 | 1/2009 | Halley |
| 2009/0036998 | A1 | 2/2009 | Finlinson et al. |
| 2009/0192619 | A1 | 7/2009 | Marlin et al. |
| 2009/0222105 | A1 | 9/2009 | Clausen |
| 2010/0094432 | A1 | 4/2010 | Mackenzie |
| 2010/0312360 | A1 | 12/2010 | Caspers |
| 2011/0046748 | A1 | 2/2011 | Martin et al. |
| 2011/0060421 | A1 | 3/2011 | Martin et al. |
| 2011/0224802 | A1 | 9/2011 | Flinlinson et al. |
| 2012/0123559 | A1 | 5/2012 | Mosler et al. |

OTHER PUBLICATIONS

Fatone, et al. "Development of Subishial Prosthetic Sockets with Vaccum-Assisted Suspension for Highly Active Persons with Transfemoral Amputations", Oct. 20, 2014.

VACUUM PUMP SYSTEMS FOR PROSTHETIC LIMBS AND METHODS OF USING THE SAME

CROSS-REFERENCE TO RELATED APPLICATION

This application claims the benefit of priority of U.S. Provisional Patent Application Ser. No. 62/214,560, filed Sep. 4, 2015 and PCT Application Serial No. PCT/US16/47775, filed Aug. 19, 2016, the disclosure of which is hereby incorporated by reference in its entirety.

CONTRACTUAL ORIGIN OF THE INVENTION

This invention was made with government support under W81XWH-10-1-0744 awarded by the U.S. Army Medical Research and Material Command. The government has certain rights in the invention.

BACKGROUND OF THE INVENTION

Field of the Invention

The present invention generally relates to suspension systems for prosthetic devices, and more particularly to vacuum pump systems for prosthetic limbs that include at least a mechanically activated pump.

Discussion of the Prior Art

Various systems have been developed for coupling a prosthetic device or prosthetic limb to a residual limb. The residual limb is connected to the prosthesis via a socket which receives and holds in place an end portion of the residual limb. Suspension is the mechanism that holds the socket to the residual limb. Vacuum is a form of suspension that uses a difference in atmospheric pressure to hold a socket to the residual limb. Liners help protect the residual limb tissue by providing cushioning and helping distribute the applied negative pressure in a uniform manner.

Vacuum pump technology is used to suspend the socket to the residual limb by creating a vacuum between the liner and the socket. The ability to maintain vacuum at a relatively consistent level can help avoid undesirable movement between the socket and the residual limb which improves comfort and avoids soft tissue damage.

Vacuum pumps fall into two categories, namely, mechanically activated or electrically activated. Electrically activated pumps tend to evacuate air more quickly, are able to monitor and adjust the vacuum pressure, and to automatically initiate pump operation if the vacuum pressure is not at least at a preselected threshold. However, electrically activated pumps include a small DC motor that requires a power source, such as disposable or rechargeable batteries. Electrically activated pumps also may generate undesirable noise.

Mechanically activated pumps use the walking motion of the user to create vacuum. One way pressure valves permit proper maintenance of vacuum pressure, without access to electricity. The necessary vacuum may be maintained indefinitely as long as there are no leaks in the system and/or the user walks occasionally. However, the mechanically activated pumps do not provide initial evacuation of air without effort, take longer to achieve operative vacuum levels, and typically need periodic motion to maintain appropriate vacuum levels. Mechanically activated pumps also tend to require a significant length for operation, as they typically operate by using a telescoping assembly. Depending on the number of parallel alignment elements involved, length can be important within a telescoping assembly, so as to provide adequate surface engagement to avoid binding. Mechanically activated pumps generally are configured for mounting below the knee because the pumps are too long to fit between the socket and the knee joint of the prosthetic limb, and as such, are not as well suited for transfemoral amputees.

Mechanically activated pumps also typically use a piston within a cylinder for pumping, or systems that include a flexible toroidal or ring-shaped reservoir or bladder that has a relatively large cylindrical telescopic tube running through the center, in place of a section of a lower limb pylon. The tube must be relatively large and of length sufficient to avoid binding, while withstanding the significant stresses encountered. In turn, the reservoir must be constructed to account for the large opening through the center.

For some users, such as military personnel with amputation who wish to return to active duty, there is an enhanced need to be able to maintain acceptable physical performance. An active soldier with amputation may be in the field for a prolonged period of time, with a need to maintain proper vacuum levels for suspension, while being without access to a power source for recharging of batteries. Thus, there exists a need for a compact, quiet, unobtrusive vacuum pump system with adjustable pressure and minimal battery recharging needs that will evacuate air from a cavity between a socket of a prosthetic limb and a residual limb.

A prior attempt to resolve this problem resulted in design of hybrid systems disclosed in U.S. patent application Ser. No. 13/529,833, the disclosure of which is incorporated by reference herein in its entirety. The designs generally include connecting together a mechanically activated pump and an electrically activated pump, with a common system controller to promote obtaining and retaining proper vacuum levels to establish and maintain suspension of a limb within a socket of a prosthetic device. However, the mechanically activated pumps disclosed in U.S. patent application Ser. No. 13/529,833 show a relatively broad bladder that may flex and bulge outward when subjected to compression, reducing the productivity of the mechanically activated pump within the system. As such, there remains a need to provide an effective, relatively low profile mechanically activated pump, and a hybrid vacuum pump system combining such a mechanically activated pump with an electrically activated pump.

The present invention addresses shortcomings in prior art vacuum pump systems for prosthetic limbs, while providing enhanced pumping systems that enable more flexible design and enhanced performance.

SUMMARY OF THE INVENTION

The purpose and advantages of the invention will be set forth in and apparent from the description and drawings that follow, as well as will be learned by practice of the claimed subject matter.

The present disclosure generally provides pump systems that include a mechanically activated pump having a lower profile design while still being able to provide vacuum within the desired range of approximately 15 mmHg to 25 mmHg. Mechanically activated pumps for use in the system utilize a diaphragm, which is domed or in the shape of a suction cup, which does not require a large central opening for a tubular telescopic assembly. By avoiding use of a toroidal bladder having a central tubular telescopic assembly, or a broad cushion-shaped bladder not having a central opening but being susceptible to flexing and bulging outward when subjected to compression, the mechanically activated pumps of the present disclosure permit use of a diaphragm having a moderate sized diameter and which requires low displacement to achieve adequate pumping capacity. Such pumps optionally permit location above or below the knee joint in a transfemoral prosthetic limb, or compact placement within a transtibial prosthetic limb.

It will be appreciated that a mechanically activated pump is a pump that requires a mechanical input, namely, movement of the prosthetic device, such as would occur for example when a user is walking. This is in contrast to an electrically activated pump that requires an electrical input from an electrical power source, such as a pump that includes an electrical motor, in the form of a reciprocating servo, a rotating motor or the like, that is powered by a battery.

In the context of the present disclosure, an electrically activated pump requires an electrical input from a power source to activate and drive an electrically driven motor. As such, while an electrical motor may contain mechanical components, it should be understood that an electrically activated pump would not include or be considered a mechanically activated pump, because that type of device requires a mechanical input via movement of the prosthetic device, which may occur, for instance, when the user walks, runs or bounces up and down on the prosthetic device while standing in place. Given that a mechanically activated pump requires physical movement of the prosthetic device to function, it is particularly advantageous to be able to use an electrically activated pump when first donning a prosthetic limb.

The mechanically activated pumps of the present disclosure may utilize first and second compression members, with a diaphragm disposed therebetween and coupling elements disposed about an outer perimeter of the diaphragm. The coupling elements permit relative translation of the compression members, which maintain a parallel relationship while compressing the diaphragm or permitting it to expand to its resting state.

To further enhance the performance of pump systems for suspension of a prosthetic limb, the present disclosure also provides pump systems that include an electrically activated pump, such as of the micro pump type utilized in exclusively electrical systems, and in the hybrid system disclosed in U.S. patent application Ser. No. 13/529,833, thereby providing a modular hybrid system. A hybrid pump system of the present design may offer a more efficient hybrid system, while still providing the significant advantages of the prior hybrid system. Such advantages include the desired rapid engagement upon initial donning of the prosthetic device, while not requiring solely battery power to evacuate air and to maintain appropriate vacuum levels. The more efficient design of the mechanically activated pump may permit longer intervals between charging of rechargeable batteries or battery packs, or between replacement of disposable batteries.

A hybrid system of the present diaphragm design also may provide for better optimization of the size and capacities of the components utilized. The new design for the mechanically activated pump portion of a hybrid system need not be as concerned with the ability to rapidly establish large capacity initial evacuation solely via the mechanically activated pump, because of the assistance of an electrically activated pump. Also, the electrically activated pump is less likely to be cycled during the course of many activities that will provide operation of a mechanically activated pump. Accordingly, depending on the length of the residual limb, it may be possible to implement a hybrid pump system of this disclosure within a system having a relatively short length, such that it could be located above or below the knee joint for a transfemoral amputee.

Thus, a hybrid system may utilize the respective strengths of mechanically and electrically activated pumps to achieve superior overall performance, while essentially also providing a redundant pump system to ensure at least adequate performance for the user. By utilizing a low profile, highly efficient mechanically activated pump design, the systems also permit placement above the knee for a transfemoral amputee, for direct interaction with a socket of a prosthetic device, if desired. The pump systems preferably have a short height, to permit positioning above the knee or elsewhere. It will be appreciated that the height may be more or less, depending on the final configuration and displacement of the mechanically activated pump, and whether or not the system includes an electrically activated pump, and if so, the hybrid configuration. This, in turn, helps avoid many of the hindrances associated with below knee systems, while permitting use of a direct connection for an inline assembly, or use of external tubing.

Accordingly, in a first aspect, disclosed herein is a mechanically activated pump for use in suspension of a prosthetic device from a residual limb. The pump includes a first compression member coupled to a second compression member, a diaphragm disposed between the first and second compression members, and coupling elements that engage and couple together the first and second compression members, wherein all of the coupling elements are disposed about an outer perimeter of the diaphragm and guide translation of the first compression member relative to the second compression member, and wherein relative movement of the first and second compression members toward each other compresses the diaphragm.

In a second aspect, disclosed herein is a method of suspending a prosthetic device from a residual limb. The method includes providing a prosthetic device having a socket that receives the residual limb. The method further includes providing a mechanically activated pump having a first compression member coupled to a second compression member, a diaphragm disposed between the first and second compression members, and coupling elements engaging and coupling together the first and second compression members, wherein all of the coupling elements are disposed about an outer perimeter of the diaphragm. The method also includes providing a pump port in communication with the socket and the diaphragm, the pump port being configured to evacuate air from the socket when operating the mechanically activated pump, and operating the mechanically activated pump when the prosthetic device is used to walk.

In a third aspect, disclosed herein is hybrid pump system for use in suspension of a prosthetic device from a residual limb. The hybrid pump system includes a mechanically activated pump, an electrically activated pump, and the mechanically activated pump and electrically activated pump are connected and each provides vacuum for use in engagement between the prosthetic device and the residual limb. The mechanically activated pump further includes a first compression member coupled to a second compression member, a diaphragm disposed between the first and second compression members, and coupling elements that engage and couple together the first and second compression members, wherein all of the coupling elements are disposed about an outer perimeter of the diaphragm and guide translation of the first compression member relative to the second compression member.

It will be appreciated that the unique mechanically activated pumps disclosed herein provide advantageous configurations that permit low profile arrangements to be utilized in suspending a prosthetic device from a residual limb. It also will be appreciated from this disclosure that a mechanically activated pump may be connected to a fluid circuit that includes an electrically activated pump, so as to create an efficient, advantageous hybrid system for use in suspension of a prosthetic device from a residual limb. It is contemplated that various configurations may be utilized and the appended claims are not to be limited to the examples illustrated.

Thus, the present disclosure presents alternatives to the prior art mechanically activated pumps, as well as to systems that use only an electrically activated pump, where the prior art systems have proven to be less effective than desired. The present disclosure also presents a novel, nonobvious improvement over the mechanically activated pumps and hybrid system disclosed in U.S. patent application Ser. No. 13/529,833, which has been incorporated herein by reference.

It is to be understood that both the foregoing general description and the following detailed description are exemplary and provided for purposes of explanation only, and are not restrictive of the subject matter claimed. Further features and objects of the present disclosure will become more fully apparent in the following description of the preferred embodiments and from the appended claims.

BRIEF DESCRIPTION OF THE DRAWINGS

In describing the preferred embodiments, reference is made to the accompanying drawing figures wherein like parts have like reference numerals, and wherein.

It should be understood that the drawings are not to scale. While some details of a pump system for a prosthetic device, including details of fastening means and other plan and section views of the particular components, have not been included, such details are considered well within the comprehension of those of skill in the art in light of the present disclosure. It also should be understood that the present invention is not limited to the example embodiments illustrated.

DETAILED DESCRIPTION OF THE PREFERRED EMBODIMENTS

Figure 1:
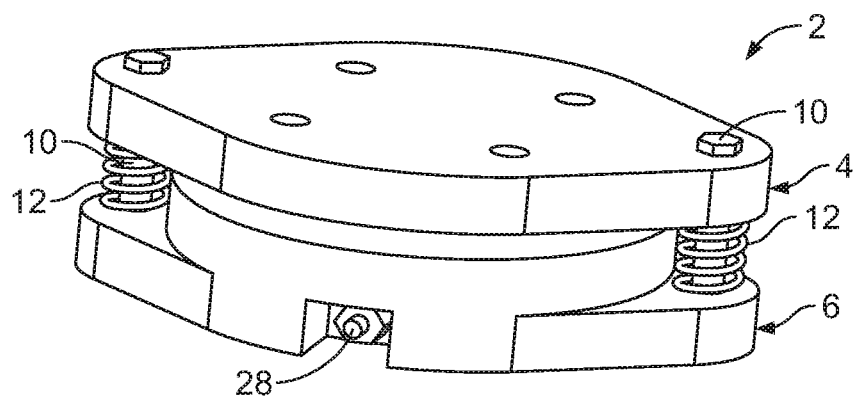
FIG. 1 is a simplified upper perspective view of an example mechanically activated pump for use in a prosthetic device.
Figure 3:
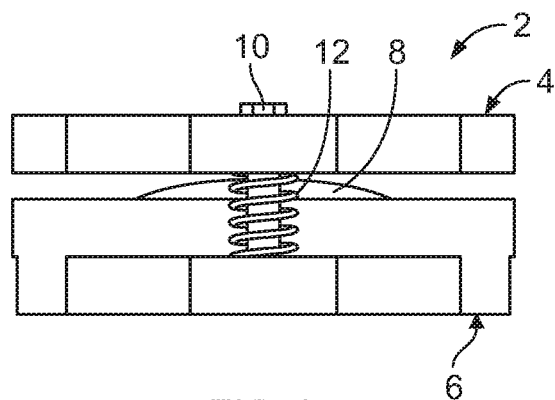
FIG. 3 is a simplified end view of the pump shown in FIG. 1.
Figure 2:
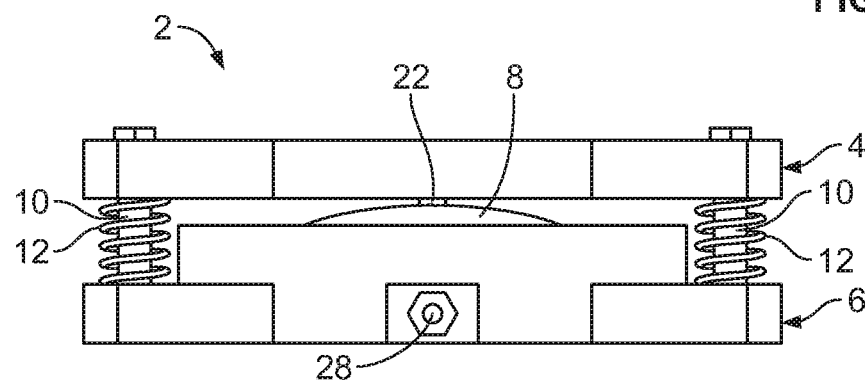
FIG. 2 is a simplified side view of the pump shown in FIG. 1.
Figure 4:
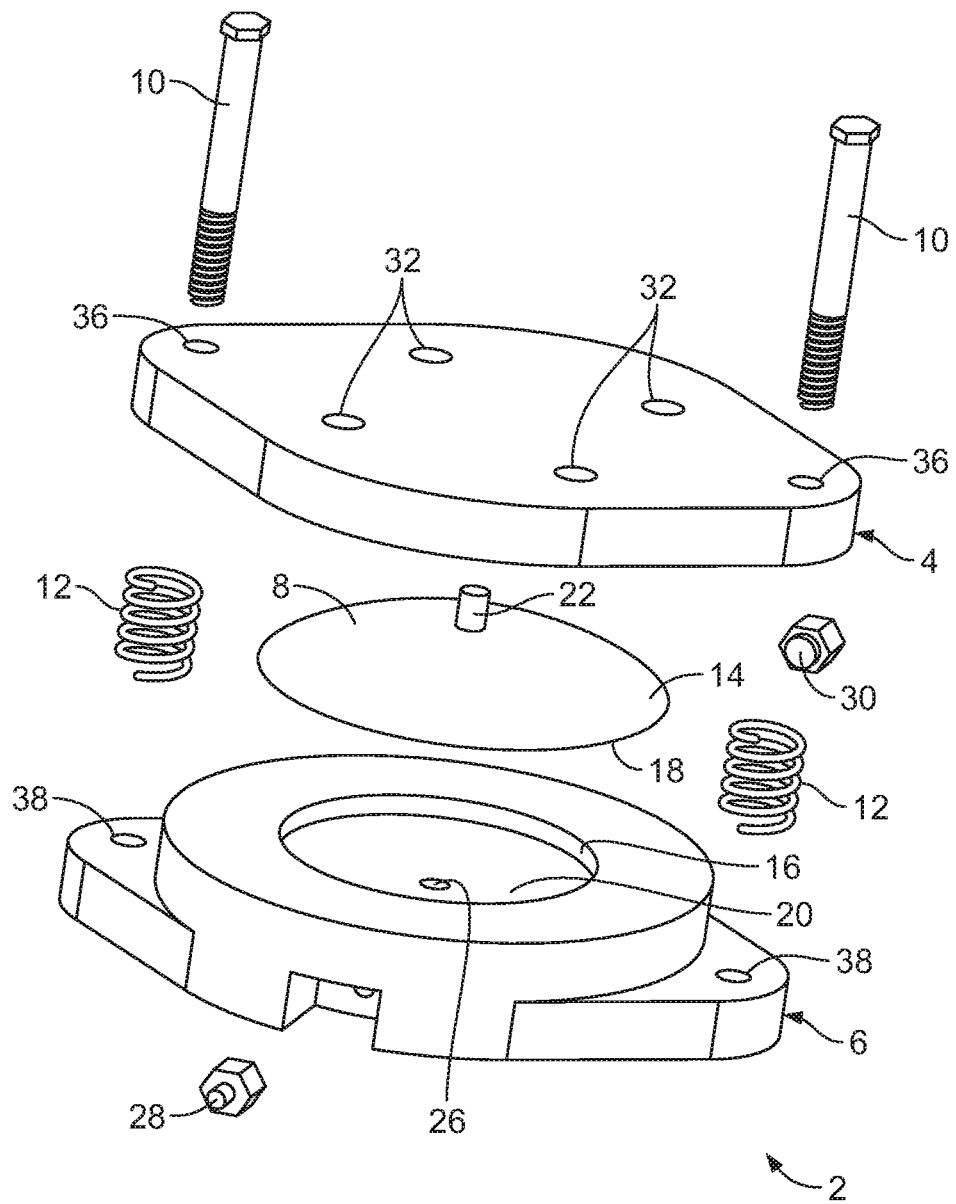
FIG. 4 is a simplified exploded upper perspective view of the pump shown in FIG. 1.
Figure 5:
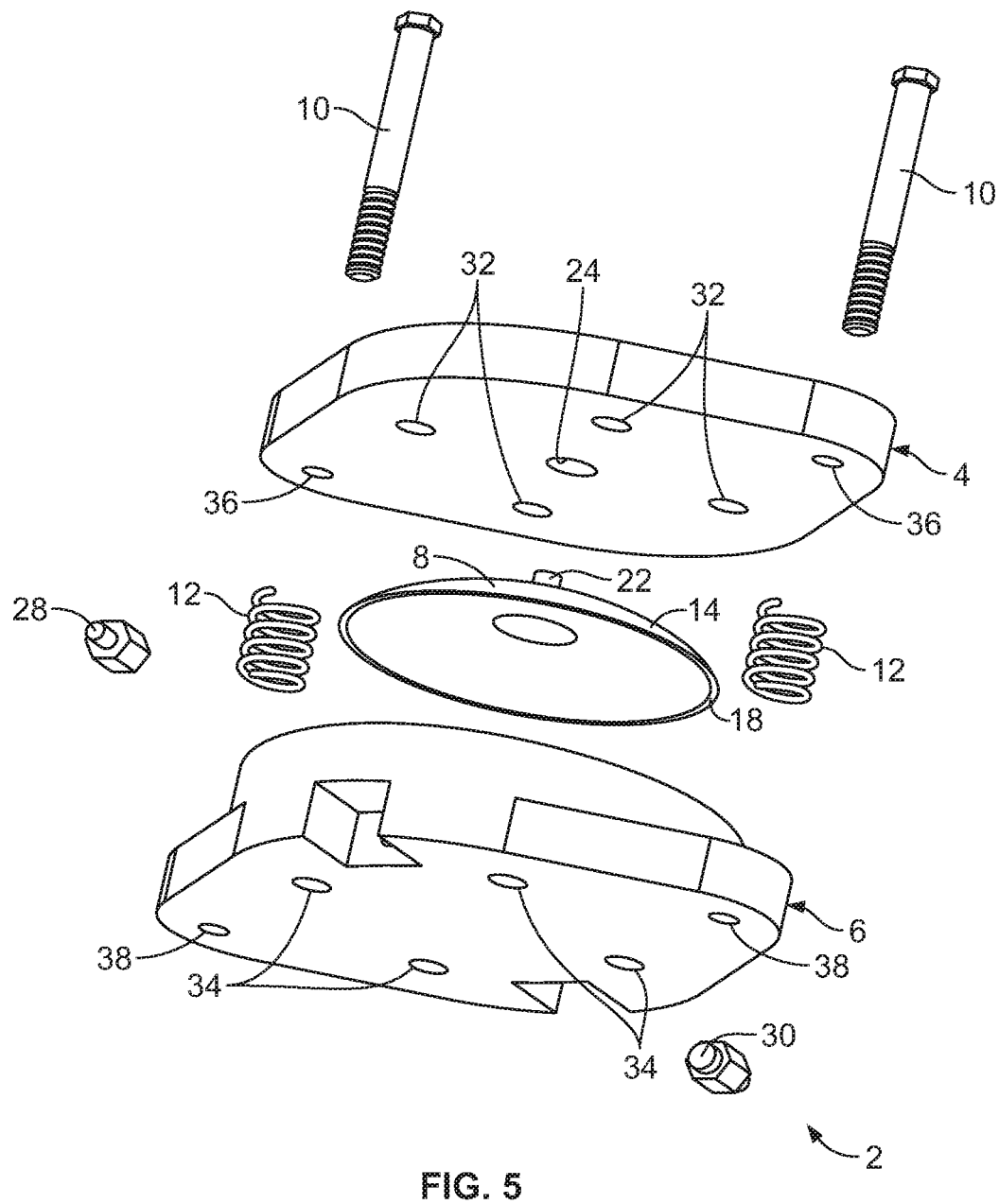
FIG. 5 is a simplified exploded lower perspective view of the pump shown in FIG. 1.
Figure 6:
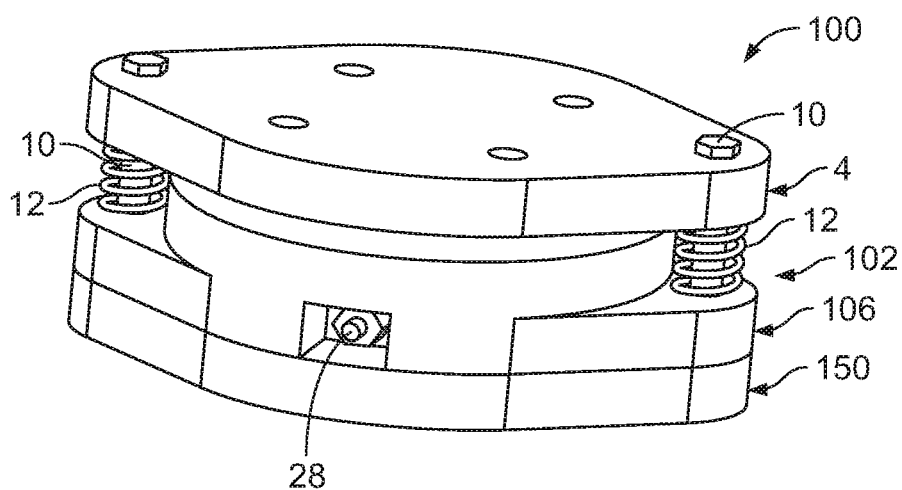
FIG. 6 is a simplified upper perspective view of an example pump system having a mechanically activated pump and an electrically activated pump for use in a prosthetic device.
Figure 8:
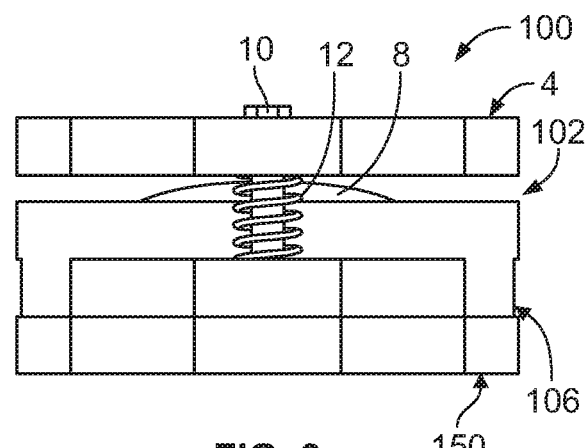
FIG. 8 is a simplified end view of the pump system shown in FIG. 6.
Figure 7:
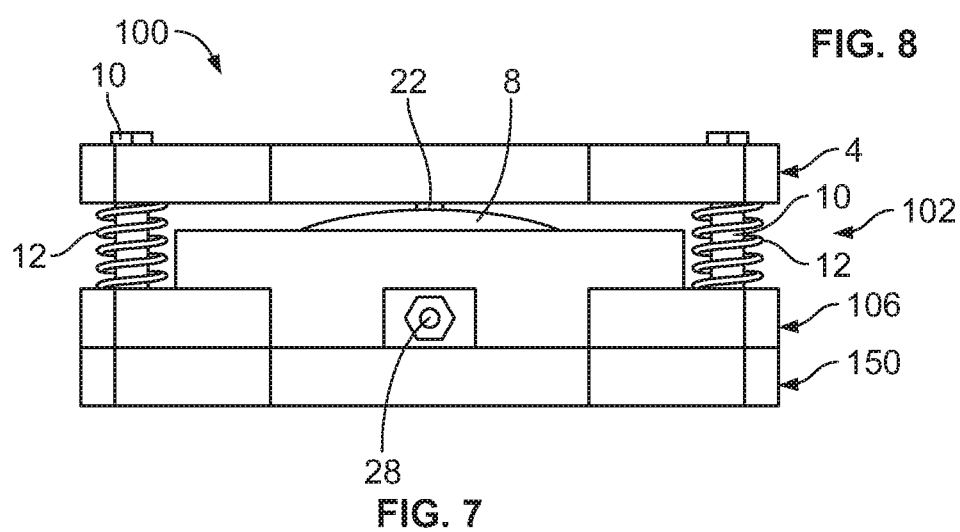
FIG. 7 is a simplified side view of the pump system shown in FIG. 6.
Figure 9:
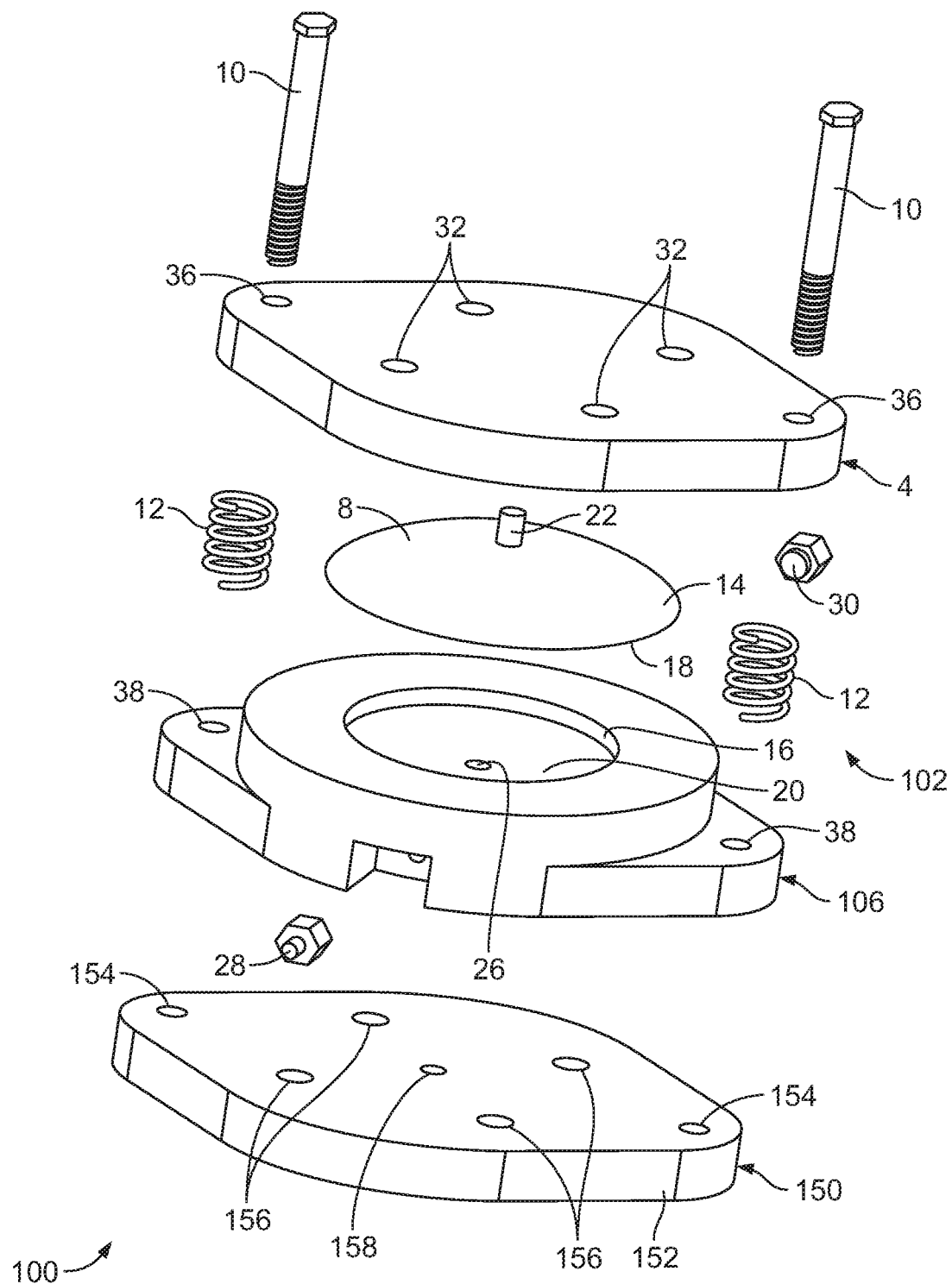
FIG. 9 is a simplified exploded upper perspective view of the pump system shown in FIG. 6.
Figure 10:
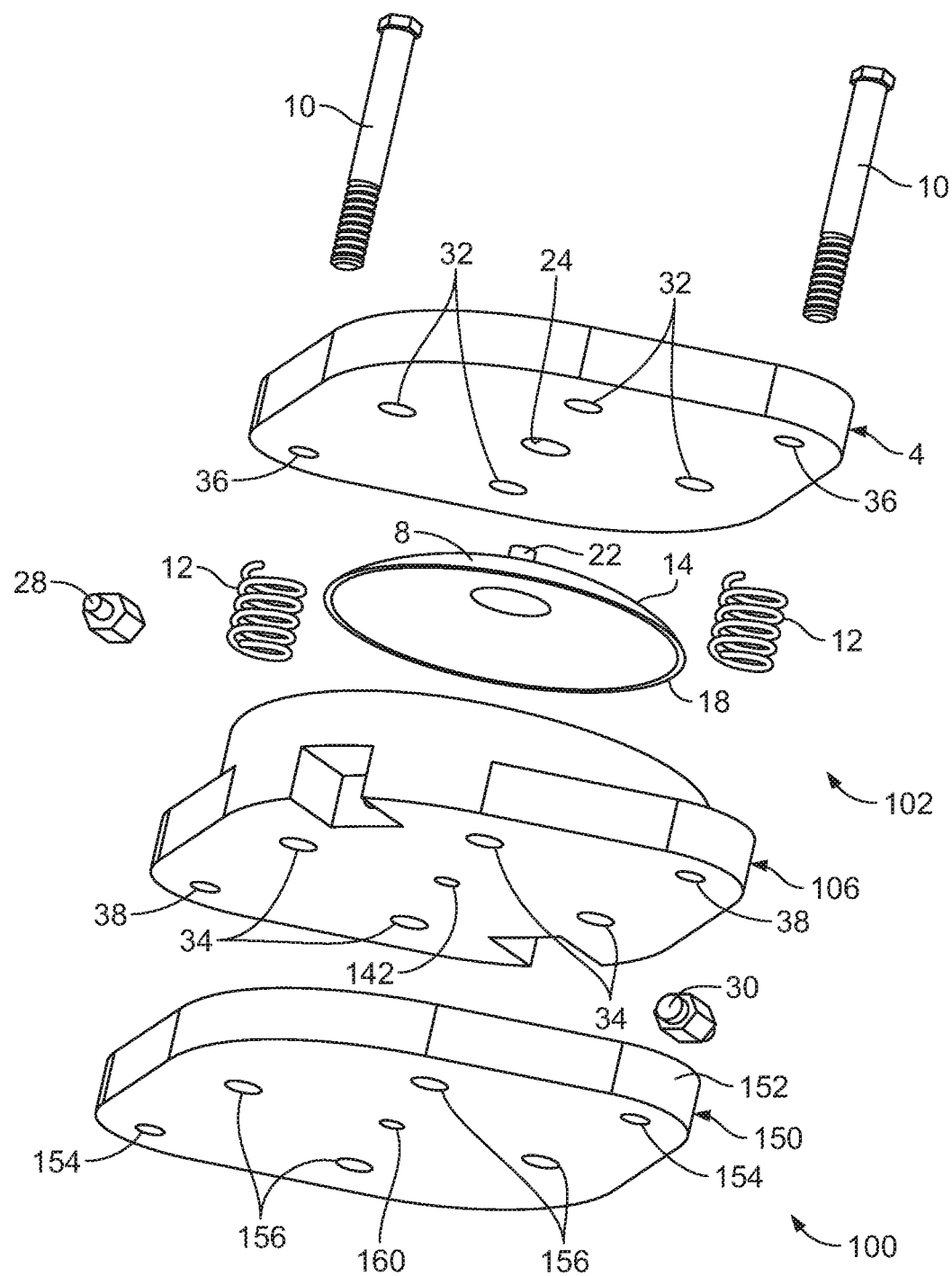
FIG. 10 is a simplified exploded lower perspective view of the pump system shown in FIG. 6.
Figure 11:
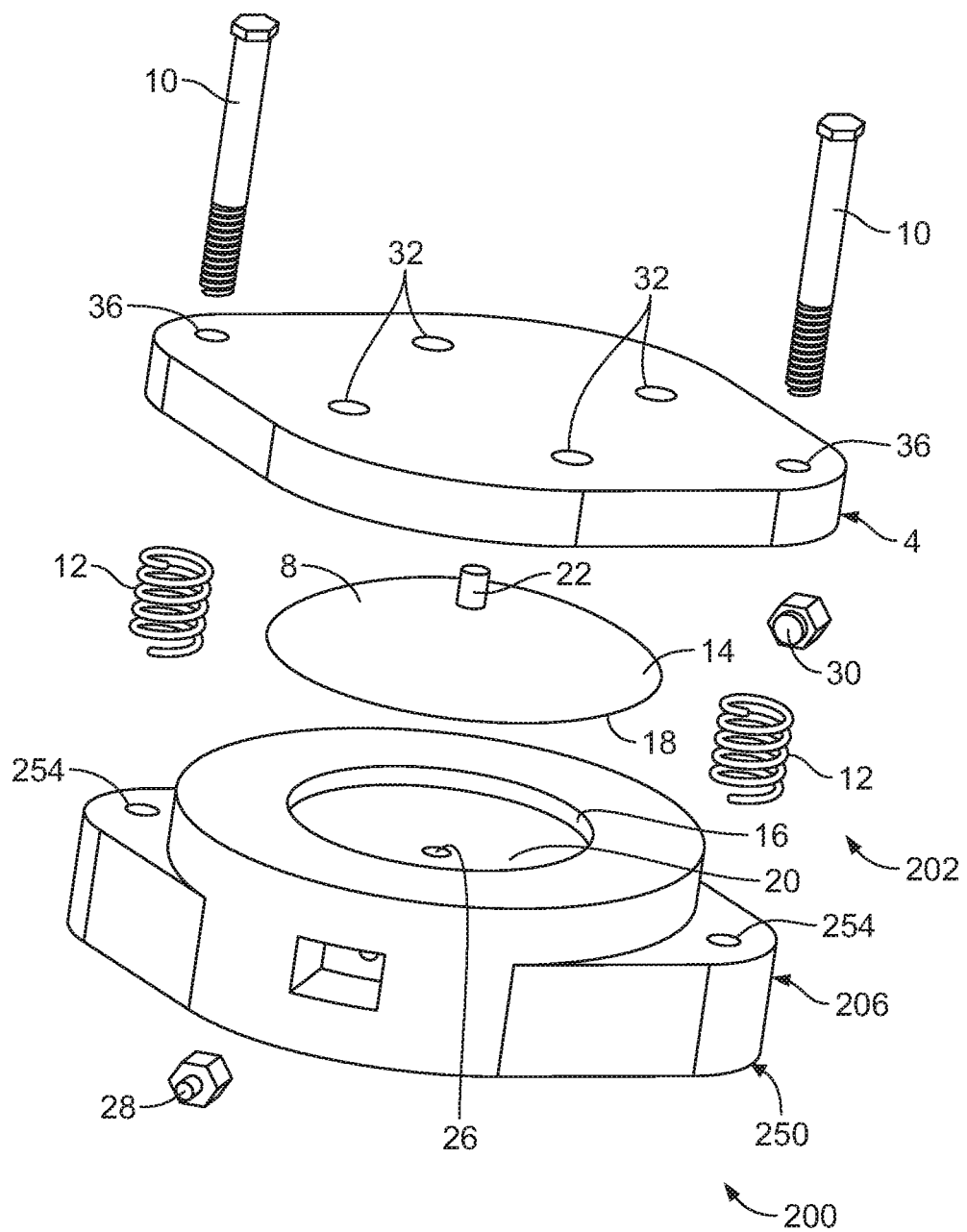
FIG. 11 is a simplified exploded upper perspective view of another example pump system having a mechanically activated pump and an electrically activated pump for use in a prosthetic device.
Figure 12:
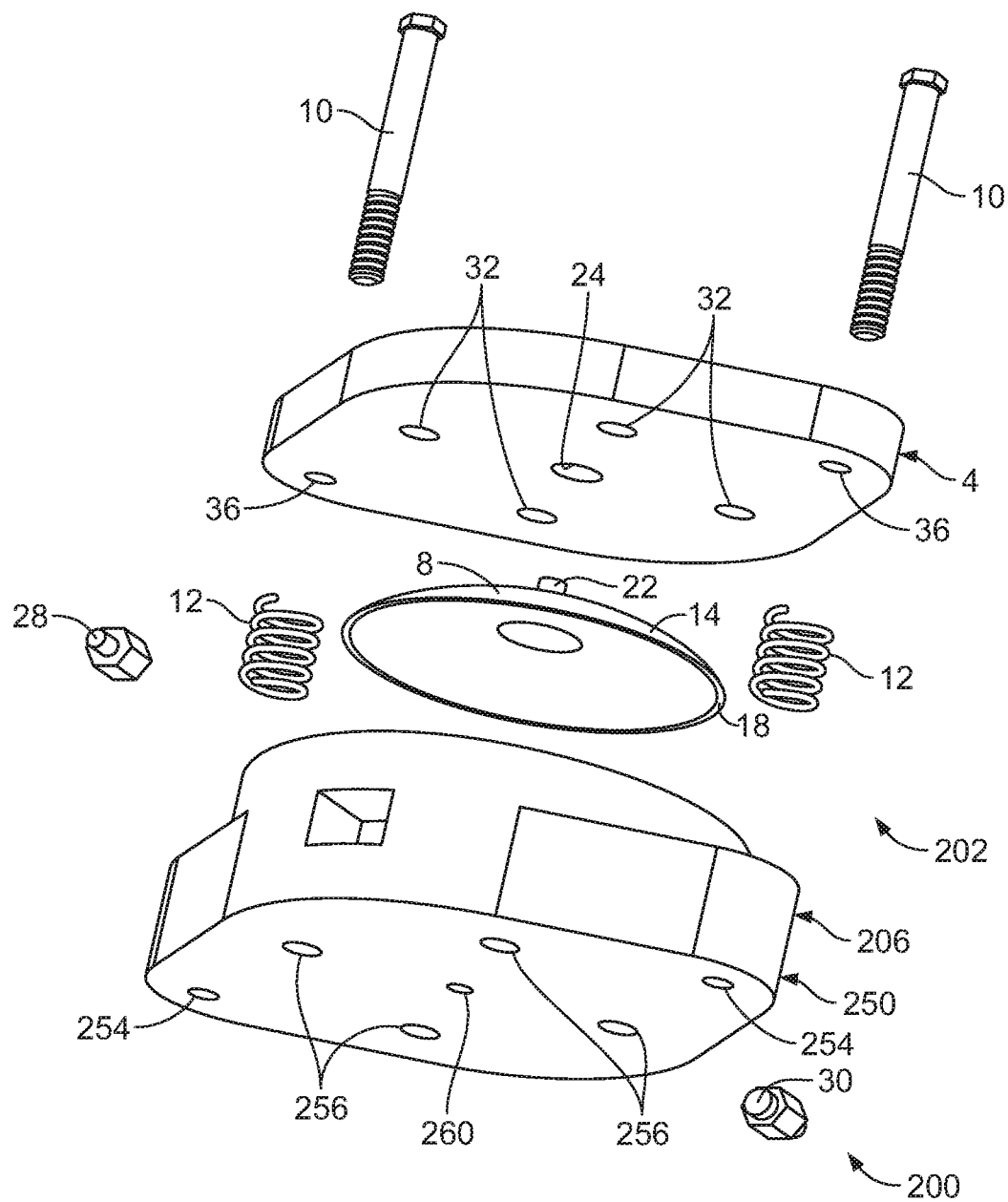
FIG. 12 is a simplified exploded lower perspective view of the pump system shown in FIG. 8.

Referring generally to FIGS. 1-12, it will be appreciated that a vacuum pump system for use in suspension of a prosthetic device from a residual limb of the present disclosure generally may be embodied within numerous configurations of pump systems. For instance, this disclosure includes example pump systems for suspending a prosthetic device from a residual limb, such as shown in FIGS. 1-5 featuring an example mechanically activated pump, or as shown in FIGS. 6-10 featuring a hybrid pump system including a mechanically activated pump that is connected to an electrically activated pump, or as shown in FIGS. 11-12 featuring another hybrid pump system including a mechanically activated pump and an electrically activated pump that have an integrated housing.

As disclosed in U.S. patent application Ser. No. 13/529, 833, it is common that a prosthetic device or limb may be provided for transfemoral or transtibial amputees. In a transfemoral configuration, such a prosthetic device generally includes a socket, a pump system, a knee joint, a pylon extending downward from the knee joint, and a prosthetic foot connected to the lower end of the pylon. The socket is open at its upper end and is adapted to receive a transfemoral residual limb, with a lower end that includes a port that is in fluid communication with the pump system.

In a transtibial configuration, the components are somewhat similar. The prosthetic device generally includes a socket, a pump system, a pylon and a prosthetic foot. However, the socket has an upper end that is open and is adapted to receive a transtibial residual limb, with a lower end that includes a port that is in fluid communication with the pump system.

Sockets of prosthetic devices having suspension systems may be constructed in numerous configurations. Some are custom molded and constructed for direct contact with the skin of the residual limb, while others are intended to receive a residual limb that is covered with one or more liner components that prevent the skin from direct contact with the socket and exposure to vacuum pressure developed within the socket. It will be appreciated that the pump systems of the present disclosure could be configured for use in prosthetic devices with either type of socket, whether for use with transfemoral or transtibial residual limbs, with the components and specifications being appropriately matched to the desired vacuum pressure. Indeed, the specific construction and shape of the socket are not at issue, and depending on the particular configuration used, the port for evacuation of air from the socket may be placed at various locations within the socket.

It will be understood that within a prosthetic device, the lower end of the socket may include a mounting flange and associated fasteners, or other connective elements, for connection to the pump system or to other intermediary components. Similarly, the upper end of a knee joint or pylon may be equipped for connection to the pump system, such as by having a mounting flange for a standard pyramid four bolt connector. It will be appreciated that the low profile, inline structure of the example pump systems herein may be incorporated into a reduced package height, which permits fluid connection of the pump system to the lower end of a socket, and may eliminate the need for external tubing. In such a configuration, a first compression member or upper compression plate of a mechanically activated pump may be molded into the lower end of a socket assembly. This would permit direct connection of a port of a mechanically activated pump with a port of the socket. Indeed, while external tubing may be used with ports that may be otherwise located on the pump system and the socket, avoiding the use of external tubing can reduce the likelihood of interference or impedance of flexion of the knee, or the risk of getting caught on a protrusion.

Turning to FIGS. 1-5, an example mechanically activated pump 2 is shown for use in a pump system to suspend a prosthetic device from a residual limb. The pump 2 of this example provides a compact, low profile, inline structure. The mechanically activated pump 2 includes a first compression member 4 coupled to a second compression member 6, with a diaphragm 8 disposed between the first and second compression members 4, 6. The pump 2 further includes coupling elements 10 that engage and couple together the first and second compression members 4, 6. The pump 2 may include two or more coupling elements, with all of the coupling elements 10 being disposed about an outer perimeter of the diaphragm 8. The coupling elements 10 guide translation of the first compression member 4 relative to the second compression member 6, and relative movement of the first and second compression members 4, 6 toward each other compresses the diaphragm 8.

The first compression member 4 is slidably coupled to the second compression member 6, and is biased to move away from the second compression member 6. The biasing of the first compression member 4 away from the second compression member 6 is provided by at least one spring 12, while the example pump 2 is shown with two springs 12.

The diaphragm 8 has a domed or suction cup shape, with a lower portion 14 of the diaphragm 8 received in a recess 16 in the upper surface of the second compression member 6. The lower portion 14 of the diaphragm 8 includes a lower surface 18 that contacts a lower surface 20 of the recess 16. The area of the lower surface 20 of the recess 16 preferably is slightly larger than the area within the perimeter of the lower surface 18 of the diaphragm 8, to account for potential movement and expansion of the diaphragm 8 during operation of the pump 2. To help keep the diaphragm 8 properly positioned within the pump 2, an upper portion 22 of the diaphragm 8 extends upward and is received within a recess 24 in the lower surface of the first compression member 4. The upper portion 22 of the diaphragm 8 may fit within the recess 24 by loose fit, press fit, threaded or other means of connection, and the recess 24 is surrounded by a surface that engages the diaphragm 8 when the first compression member 4 is moved toward the second compression member 6, to force air outward from a volume defined between the diaphragm 8 and the lower surface 20 of the recess 16 in the second compression member 6. The lower surface of the first compression member 4 may be configured to interact with the outer surface of the diaphragm 8, and in this example, the lower surface is generally planar surface.

A fluid circuit permits evacuation of a socket of a prosthetic device by having the second compression member 6 of the mechanically activated pump 2 include at least one port 26 that is used to fluidly connected the socket to the volume defined between the diaphragm 8 and the lower surface 20 of the recess 16. Positioned between the port 26 and the socket is at least one one-way valve 28, which in this example is shown in a position where it is connected to the second compression member 6. Thus, this example pump 2 may use a section of tubing to connect the one-way valve 28 to an evacuation port in a socket of a prosthetic device. The volume defined between the diaphragm 8 and the lower surface 20 of the recess 16 also is fluidly connected to at least one output one-way valve 30, which provides an exhaust port for the pump 2 to expel the air to the atmosphere as the diaphragm 8 is being compressed, so that it can then evacuate air from the socket as the diaphragm 8 returns to its normal pre-compressed shape.

The mechanically activated pump 2 may be structurally incorporated into a prosthetic device by connecting the first compression member 4 to a socket of the prosthetic device, either by use of various fasteners, such as by use of screws that may engage the first compression member 4 at the apertures 32, or by molding or laminating the first compression member 4 into the lower end of the socket. The pump 2 also may be connected at the second compression member 6 to a portion of a knee joint or pylon by use of various fasteners. Mounting apertures 34 in the second compression member 6 are configured to permit fasteners to pass therethrough for mounting to a standard pyramid four bolt connector at the upper end of a knee joint 8 or pylon, although it will be appreciated that other mounting interfaces and hardware may be utilized. In this example, the first compression member 4 also includes apertures 36 that slidably receive the coupling elements 10, in the form of bolts having smooth shafts and threaded distal ends. The threaded distal ends of the coupling elements 10 threadably engage further apertures 38 in the second compression member 6 to couple the first and second compression members 4, 6, while capturing the diaphragm 8 therebetween.

The first and second compression members 4, 6 preferably are constructed of relatively light weight, generally rigid, suitable metals, such as aluminum alloys, titanium alloys, stainless steels or superalloys, or various plastics or composite materials. The second compression member 6 preferably also is constructed of a non-porous material and/or may include a sealant or coating on its upper surface that will be in contact with the air being evacuated from a socket. Depending on the environment to which a prosthetic device may be subjected, it may be desirable for the materials to be waterproof, sand-proof, and weather and corrosion resistant, although an outer pump system cover also may be employed to reduce the likelihood of intrusion of fluids or foreign matter.

While the coupling elements may be of a different configuration and size, the mechanically activated pump 2 should provide sufficient structural integrity and stability to maintain a consistent and predictable gait and resistance to torsional inputs, such as a twisting motion after planting a step. Also, it will be appreciated that the at least one spring might be incorporated into the coupling elements or located within or around the diaphragm, as opposed to using the separate springs 12 shown in the first example. A normal step by the user will cause the first compression member 4 to translate toward the second compression member 6, overcoming the biasing provided by the at least one spring 12 and contacting and partially compressing the diaphragm 8. The at least one spring also provides some shock absorption.

The diaphragm 8 may be particularly effective, while being of relatively short height because it does not require a pylon to pass through the center of the diaphragm 8, and avoids a tendency to bulge instead of drive air outward, which may be present in the use of a balloon-like bladder. The pump 2 may have a relatively broad configuration, whether located above the knee in a transfemoral configuration or below the knee in a transtibial configuration.

The diaphragm 8 generally is a dome or suction cup shaped, elastomeric body, and depending on the extent of the desired inherent rebound within the structure, and the anticipated environmental conditions, may be constructed of various rubbers, such as plasticized Halobutyl or polysulphide rubbers, plastics, such as ABS, PEEK or other polymers, Nylon, composites or other suitable materials. The diaphragm 8 also may be constructed of one or more materials and in a manner that will tend to return it to its original shape, after having been compressed, thereby helping to separating the first and second compression members 4, 6. Thus, by the diaphragm 8 and/or use of one or more springs, rebound and expansion of the diaphragm is assured during repeated compression movements that occur during walking, running or isolated bouncing-type movements. Also, it will be appreciated that many alternative configurations for compression members, diaphragms, coupling elements, springs and valves may be used in suitable alternative structures.

Turning to FIGS. 6-10, a first example hybrid pump system 100 is shown for use in suspension of a prosthetic device from a residual limb. The first example hybrid pump system 100 includes a mechanically activated pump 102 and an electrically activated pump 150. The mechanically activated pump 102 is similar to the previously described mechanically activated pump 2, except for the substitution of a second compression member 106 for the second compression member 6. The substitute second compression member 106 is identical to the second compression member 6 except for the inclusion of a port 142 that extends downward to fluidly connect the port 26 to a port of the electrically activated pump 150. The electrically activated pump 150 has a housing 152 and includes threaded apertures 154 for connection to the coupling elements 10, and apertures 156 to capture the electrically activated pump 150 between the second compression member 106 and structural component of a prosthetic device, such as a pyramid mount of a pylon, a port 158 through the upper surface of the housing 152 for connection to the port 26 in the bottom of the second compression member 106 of the mechanically activated pump 102, and a port 160 in the lower surface of the housing 152 as an exhaust port from which the electrically activated pump 150 may expel air that has been withdrawn from the socket of a prosthetic device.

In the first example hybrid pump system 100, the electrically activated pump 150 is vertically stacked or positioned in-line with and connected to the second compression member 106 of the mechanically activated pump 102. As may be seen in a simplified manner in FIGS. 6-10, the electrically activated pump 150 includes a housing 152 which is fluidly connected to the ports and valves of that are connected to the second compression member 106. It will be appreciated that the electrically activated pump 150 may be equipped with alternative valving and operative features, as desired. Also, the housing 152 of the electrically activated pump 150 alternatively could be configured to be integrated into the lower end of a socket, above the mechanically activated pump 102, or could be configured to be located along a side of the mechanically activated pump, as opposed to being in a vertically stacked relationship.

It will be appreciated that the housing 152 may contain the necessary electrical components of the pump, as disclosed in U.S. patent application Ser. No. 13/529,833. The example layouts and functional schematics therein also would apply to the basic function and connection of the hybrid pump system 100. The electrical components of the electrically activated pump may include conventional components and be connected by suitable tubing and wiring, leads or other circuitry, to meet the needs and satisfy the design specifications and constraints within a particular implementation. Thus, the components may include a microcontroller that includes a circuit board and is connected to a motorized pump, a pressure sensor, and a battery. A user interface, in the form of an on/off button may be located on the housing 152 and be connected to the microcontroller. An optional serial data port also may be utilized to interact with the microcontroller, such as to track and record the operating conditions of the pump system, for diagnostic and historical monitoring purposes.

Similarly to the hybrid system disclosed in U.S. patent application Ser. No. 13/529,833, the hybrid pump system 100 may include a further user interface, such as in the form of a wireless remote control device, a personal data assistant device, a laptop or tablet computer, a cell phone or other wireless apparatus, which may be utilized to interact with the microcontroller to input particular settings that are associated with performance parameters, such as the minimum and maximum vacuum pressures between which the system will operate, the battery charge level at which a warning light or alarm may be emitted, or to adjust other parameters that would be desirable to control. The further user interface also may be used to display information associated with the present status of the system, such as the current vacuum pressure level, battery charge level, or predictive information, such as the battery life remaining or time interval until the next regular maintenance is recommended. The hybrid pump system 100 may include warning lights or alarms that may be connected to the housing 152, or embodied within the further user interface, to alert a user to important information.

Also similar to the disclosure of U.S. patent application Ser. No. 13/529,833, the battery of the hybrid pump system 100 may be rechargeable, such as by direct or indirect connection to a power charge device. The battery also may be replaceable, so as to permit one or more spare, charged batteries to be utilized during periods of extended use away from a power recharging source. It will be appreciated that the battery may simply be of a disposable type, or that there could be an interface to permit interchangeability between a rechargeable battery and a disposable battery, based on the convenience and circumstances faced by the user.

It will be appreciated that the hybrid pump system 100 presents a modular system that can be utilized in a number of ways, similar to those described in the schematics provided in U.S. patent application Ser. No. 13/529,833. For example, when a residual limb of a user is received in a socket of a prosthetic device, the user must act to overcome the unevacuated chamber presented by the socket. The user may take one of two actions, namely, first to engage the electrically activated pump 150 via a user interface or to move with the prosthetic limb in a manner that would provide mechanical power to the mechanically activated pump 102. The two different actions both cause the pump system 100 to provide a response by which air is withdrawn from the socket and expelled to the atmosphere.

Thus, the mechanically activated pump 102 or the electrically activated pump 150 may be used to evacuate air from the socket, with the understanding that either pump may be used exclusively, if need be. However, maximum comfort and convenience can be achieved by first utilizing the electrically activated pump 150 to establish rapid initial evacuation, and thereafter the user may rely on the mechanically activated pump 150, if the user is actively moving, such as walking, running or able to impose at least a bouncing motion on the prosthetic limb, or if the user happens to be inactive at a time when further evacuation of air is needed, the monitoring system within the electrically activated pump may automatically engage the motorized pump to reestablish an acceptable vacuum pressure.

The incorporated disclosure also provides a schematic representation that would apply to the present hybrid pump system 100 when a user is walking and the pump hybrid system 100 is within an electrical pump-vacuum control range. Thus, within a swing phase, the first and second compressible members 4, 106 move away from each other, allowing the diaphragm 8 to expand and draw air from the socket. Meanwhile, the electrically activated pump 150 may draw air from the socket and expel the air to the atmosphere through the output valve 30. Within the stance phase, the first compression member 4 translates relative to the second compression member 106 to compress the diaphragm 8, expelling the air previously withdrawn from the socket, while the electrically activated pump 150 is able to continue to operate in the same manner as during the swing phase.

The incorporated disclosure further provides a schematic representation that would apply to the present hybrid pump system 100 when a user is walking and the hybrid pump system 100 is outside of an electrical pump-vacuum control range. Within a swing phase, the first and second compressible members 4, 106 again move away from each other, allowing the diaphragm 8 to expand and draw air from the socket. Meanwhile, the electrically activated pump 150 is not energized, to save battery charge. Within a stance phase, the first compression member 4 translates relative to the second compression member 106 to compress the diaphragm 8, expelling the air previously withdrawn from the socket.

From the foregoing description, it will be appreciated that a method of suspending a prosthetic device from a residual limb is provided herein. The method includes providing a prosthetic device having a socket that receives the residual limb. The method further includes providing a mechanically activated pump having a first compression member coupled to a second compression member, a diaphragm disposed between the first and second compression members. The coupling elements engage and couple together the first and second compression members, wherein all of the coupling elements are disposed about an outer perimeter of the diaphragm, such that the coupling elements are at or beyond the outer perimeter of the diaphragm. The method also includes fluidly connecting the socket and the diaphragm in a fluid circuit that is configured to evacuate air from the socket when operating the mechanically activated pump. Operation of the mechanically activated pump occurs when the prosthetic device is used to walk or otherwise include up and down motion. It will be appreciated that a method of suspending a prosthetic device from a residual limb also is provided herein with respect to use of an electrically activated pump.

Turning to FIGS. 11-12, a second example hybrid pump system 200 is disclosed for use in suspending a prosthetic device from a residual limb. The hybrid pump system 200 is quite similar to the first example hybrid pump system 100, but varies somewhat in that the second compression member 206 incorporates the housing of the electrically activated pump 250. Thus, the second example hybrid pump system 200 reduces the number of larger housing components by including in the second compression member 206 an electrically activated pump 250. This may also reduce the overall height of the hybrid pump system 200 and may provide a more efficient use of space for the fluid circuit that fluidly connects the mechanically activated pump 202 and the electrically activated pump 250, while providing a one-way valve 28 for connection to the socket of a prosthetic device. The substitute second compression member 206 includes threaded apertures 254 for connection to the coupling elements 10, and apertures 256 to connected the second compression member 206 to a structural component of a prosthetic device, such as a pyramid mount of a pylon, and a port 260 in the lower surface of the lower compression member 206 as an exhaust port from which the electrically activated pump 250 may expel air that has been withdrawn from the socket of a prosthetic device.

The hybrid pump system 200 otherwise operates in a similar manner to that of the hybrid pump system 100. As was noted with respect to the first example hybrid pump system 100, the second example hybrid pump system 200 optionally could locate the electrically activated pump outward from the perimeter of the diaphragm of the mechanically activated pump, so as to further reduce the height of the pump system.

It will be appreciated that the electrical components of the electrically activated pump 250 may be similar and have similar basic functions and connection configurations to those described above with respect to the first example hybrid pump system 100. It also will be appreciated that the components may be configured and connected in fluid communication by conventional means, such as by suitable tubing, and/or may be configured and connected electrically by conventional means, such as by suitable wires, leads or other circuitry, so as to meet the needs and satisfy the design specifications and constraints within of a particular implementation. The description set forth with respect to the structures and methods of operation of the mechanically activated pump 2, and the combination of the mechanically activated pump 102 and electrically activated pump 150 also would apply to the second hybrid pump system 200 to establish and maintain an evacuated chamber in the socket of a prosthetic device, whether the mechanically activated pump is used alone, or is operationally paired with the electrically activated pump.

It will be appreciated that a pump system for use in suspension of a prosthetic device from a residual limb in accordance with the present disclosure may be provided in various configurations. Any variety of suitable materials of construction, configurations, shapes and sizes for the components and methods of connecting the components may be utilized to meet the particular needs and requirements of an end user. It will be apparent to those skilled in the art that various modifications can be made in the design and construction of such pump systems without departing from the scope or spirit of the claimed subject matter, and that the claims are not limited to the preferred embodiments illustrated herein.

What is claimed is:

1. A hybrid pump system for use in suspension of a prosthetic device from a residual limb comprising:
   a mechanically activated pump;
   an electrically activated pump;

the mechanically activated pump and electrically activated pump being connected and each provides vacuum for use in engagement between the prosthetic device and the residual limb;

the mechanically activated pump further comprising:
- a first compression member coupled to a second compression member;
- a diaphragm disposed between the first and second compression members, wherein the electrically activated pump is disposed outward from an outer perimeter of the diaphragm; and
- coupling elements that engage and couple together the first and second compression members, wherein all of the coupling elements are disposed about the outer perimeter of the diaphragm and guide translation of the first compression member relative to the second compression member.

2. The hybrid pump system in accordance with claim 1, wherein the first compression member is slidably coupled to the second compression member.

3. The hybrid pump system in accordance with claim 1, wherein the first compression member is biased to move away from the second compression member.

4. The hybrid pump system in accordance with claim 3, wherein at least one spring provides the biasing of the first compression member away from the second compression member.

5. The hybrid pump system in accordance with claim 1, wherein the diaphragm has a domed shape.

6. The hybrid pump system in accordance with claim 1, wherein a lower portion of the diaphragm is received in a recess of the second compression member.

7. The hybrid pump system in accordance with claim 1, wherein an upper portion of the diaphragm is received in a recess of the first compression member.

8. The hybrid pump system in accordance with claim 1, wherein the electrically activated pump further comprises a battery.

9. The hybrid pump system in accordance with claim 1, wherein the battery is rechargeable.

10. The hybrid pump system in accordance with claim 1, wherein the electrically activated pump is disposed above or below the mechanically activated pump.

* * * * *